United States Patent
Dipietro et al.

(10) Patent No.: US 9,180,194 B2
(45) Date of Patent: *Nov. 10, 2015

(54) METHOD AND COMPOSITION FOR TRANSDERMAL DRUG DELIVERY

(71) Applicant: Acrux DDS Pty Ltd, West Melbourne, Victoria (AU)

(72) Inventors: Tony Dipietro, Templestowe Lower (AU); Andrew Humberstone, Vaud (CH); Igor Gonda, South Yarra (AU); Adam Watkinson, Lympne (GB); Kerrie Setiawan, South Yarra (AU); Nina Wilkins, Kensington (AU)

(73) Assignee: ACRUX DDS PTY LTD, West Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/509,404

(22) Filed: Oct. 8, 2014

(65) Prior Publication Data

US 2015/0087623 A1  Mar. 26, 2015

Related U.S. Application Data

(63) Continuation of application No. 12/823,448, filed on Jun. 25, 2010, now Pat. No. 8,993,520, which is a continuation of application No. 11/445,463, filed on Jun. 2, 2006, now Pat. No. 8,435,944.

(60) Provisional application No. 60/752,884, filed on Dec. 23, 2005.

(30) Foreign Application Priority Data

Jun. 3, 2005 (AU) ................................ 2005902902

(51) Int. Cl.
*A61K 38/00* (2006.01)
*A61P 5/24* (2006.01)
*A61K 47/10* (2006.01)
*A61K 9/00* (2006.01)
*A61K 47/12* (2006.01)
*A61K 47/32* (2006.01)
*A61K 31/568* (2006.01)
*A61K 47/14* (2006.01)

(52) U.S. Cl.
CPC .............. *A61K 47/10* (2013.01); *A61K 9/0014* (2013.01); *A61K 31/568* (2013.01); *A61K 47/12* (2013.01); *A61K 47/14* (2013.01); *A61K 47/32* (2013.01)

(58) Field of Classification Search
CPC ... A61K 47/10; A61K 31/195; A61K 31/198; A61K 31/355; A61K 31/56; A61K 31/568; A61K 47/12; A61K 47/32; A61K 31/4468; A61K 31/485; A61K 47/183; A61K 47/24; A61K 47/34; A61K 8/361; A61K 8/69; A61K 9/06; A61K 9/703; A61K 9/7038; A61K 9/7081; A61K 9/7092; A61K 38/08; A61K 8/34; A61K 8/411; A61K 8/63; A61K 8/61; A61K 8/8176; A61K 9/08; A61K 9/7023

See application file for complete search history.

(56) References Cited

U.S. PATENT DOCUMENTS

| | | |
|---|---|---|
| 4,264,586 A | 4/1981 | Callingham et al. |
| 4,824,676 A | 4/1989 | Bodor |
| 5,008,111 A | 4/1991 | Bodor |
| 5,118,494 A | 6/1992 | Schultz et al. |
| 5,122,383 A | 6/1992 | Heiber et al. |
| 5,254,338 A | 10/1993 | Sakai et al. |
| 5,378,451 A | 1/1995 | Gorman et al. |
| 5,613,958 A | 3/1997 | Kochinke et al. |
| 5,780,050 A | 7/1998 | Jain et al. |
| 5,788,983 A | 8/1998 | Chien et al. |
| 5,792,469 A | 8/1998 | Tipton et al. |
| 5,855,920 A | 1/1999 | Chein |
| 5,962,505 A | 10/1999 | Bobrove et al. |
| 5,968,919 A | 10/1999 | Samour et al. |
| 6,010,716 A | 1/2000 | Saunal et al. |
| 6,211,250 B1 | 4/2001 | Tomlinson et al. |
| 6,238,284 B1 | 5/2001 | Dittgen et al. |
| 6,299,900 B1 | 10/2001 | Reed et al. |
| 6,387,383 B1 | 5/2002 | Dow et al. |
| 6,475,467 B1 | 11/2002 | Keller et al. |
| 6,503,894 B1 | 1/2003 | Dudley et al. |
| 6,562,790 B2 | 5/2003 | Chien et al. |

(Continued)

FOREIGN PATENT DOCUMENTS

| | | |
|---|---|---|
| EP | 0 349 763 | 1/1990 |
| EP | 1 541 125 | 6/2005 |

(Continued)

OTHER PUBLICATIONS

Morgan et al., "Transdermal Delivery of Estradiol in Postmenopausal Women with a Novel Topical Aerosol," *Journal of Pharmaceutical Sciences*, vol. 87, No. 10, pp. 1226-1228, Oct. 1998.

(Continued)

*Primary Examiner* — Lezah Roberts
*Assistant Examiner* — Nannette Holloman
(74) *Attorney, Agent, or Firm* — Foley & Lardner LLP

(57) ABSTRACT

The invention is directed to a transdermal drug delivery composition which includes at least one physiologically active agent; and at least one volatile solvent; and at least one viscosity modulating agent. The invention extends to methods of administering such a composition to a subject and treatment of subjects using the composition.

6 Claims, 4 Drawing Sheets

(56) References Cited

U.S. PATENT DOCUMENTS

| | | | |
|---|---|---|---|
| 6,682,757 | B1 | 1/2004 | Wright |
| 6,743,448 | B2 | 6/2004 | Kryger |
| 6,818,226 | B2 | 11/2004 | Reed et al. |
| 6,902,741 | B1 | 6/2005 | Grawe et al. |
| 6,916,486 | B2 | 7/2005 | Klose et al. |
| 6,916,487 | B2 | 7/2005 | Klose et al. |
| 6,923,983 | B2 | 8/2005 | Morgan et al. |
| 6,929,801 | B2 | 8/2005 | Klose et al. |
| 6,964,777 | B2 | 11/2005 | Klose et al. |
| 6,998,138 | B2 | 2/2006 | Chew et al. |
| 7,094,422 | B2 | 8/2006 | Chew et al. |
| 7,387,789 | B2 | 6/2008 | Klose et al. |
| 7,438,203 | B2 | 10/2008 | Reed et al. |
| 7,608,282 | B2 | 10/2009 | Altenschöpfer et al. |
| 8,071,075 | B2 | 12/2011 | Reed et al. |
| 8,435,944 | B2 | 5/2013 | Dipietro et al. |
| 2001/0051157 | A1 | 12/2001 | Breton et al. |
| 2002/0150625 | A1 | 10/2002 | Kryger |
| 2003/0199584 | A1 | 10/2003 | Ahluwalia et al. |
| 2004/0009214 | A1 | 1/2004 | Klose et al. |
| 2004/0081685 | A1 | 4/2004 | Wright, IV |
| 2004/0126355 | A1 | 7/2004 | Childers |
| 2004/0175416 | A1 | 9/2004 | Taravella et al. |
| 2005/0002868 | A1 | 1/2005 | Gonda et al. |
| 2005/0020552 | A1 | 1/2005 | Aschkenasy et al. |
| 2005/0025833 | A1 | 2/2005 | Aschkenasy et al. |
| 2005/0042268 | A1 | 2/2005 | Aschkenasy et al. |
| 2005/0049233 | A1 | 3/2005 | Dudley |
| 2005/0181032 | A1 | 8/2005 | Wilkins et al. |
| 2005/0186141 | A1 | 8/2005 | Gonda et al. |
| 2005/0196414 | A1 | 9/2005 | Dake et al. |
| 2006/0153905 | A1 | 7/2006 | Carrara et al. |
| 2007/0071803 | A1 | 3/2007 | Reed et al. |
| 2007/0275943 | A1 | 11/2007 | Morgan et al. |
| 2007/0293842 | A1 | 12/2007 | Knight et al. |
| 2008/0131494 | A1 | 6/2008 | Reed et al. |
| 2008/0152597 | A1 | 6/2008 | Reed et al. |
| 2010/0166674 | A1 | 7/2010 | Morgan et al. |
| 2010/0322884 | A1 | 12/2010 | Dipietro et al. |

FOREIGN PATENT DOCUMENTS

| | | |
|---|---|---|
| GB | 1 192 003 | 5/1970 |
| GB | 1192003 | 5/1970 |
| GB | 1 258 394 | 12/1971 |
| JP | 2001-270826 | 10/2001 |
| WO | WO 93/25168 A1 | 12/1993 |
| WO | WO 95/05164 | 2/1995 |
| WO | WO 97/29735 | 8/1997 |
| WO | WO 99/20257 A1 | 4/1999 |
| WO | WO 99/24041 A1 | 5/1999 |
| WO | WO 00/45795 A2 | 8/2000 |
| WO | WO 00/47191 | 8/2000 |
| WO | WO 02/17927 A1 | 3/2002 |
| WO | WO 02/17967 A1 | 3/2002 |
| WO | WO-03/061554 A2 | 7/2003 |
| WO | WO 03/086331 | 10/2003 |
| WO | WO 2004/069141 A2 | 8/2004 |
| WO | WO 2004/080413 A2 | 9/2004 |
| WO | WO 2004/091631 A1 | 10/2004 |
| WO | WO 2005/039531 A1 | 5/2005 |
| WO | WO 2005/049026 A1 | 6/2005 |
| WO | WO 2006/027278 A1 | 3/2006 |
| WO | WO 2006/094193 A2 | 9/2006 |
| WO | WO 2006/094263 A2 | 9/2006 |

OTHER PUBLICATIONS

Morgan et al., "Enhanced Transdermal Delivery of Sex Hormones in Swine with a Novel Topical Aerosol," *Journal of Pharmaceutical Sciences*, vol. 87, No. 10, pp. 1219-1225, Oct. 1998.

Sundaram et al., "7-Methyl-Nortestosterone (MENT): The Optiaml Androgen for Male Contraception," *An. Med.*, vol. 25, No. 2, pp. 199-205, Jan. 1, 1993.

Cowan-Ellsberry et al., "Axilla surface area for males and females: Measured distribution," *Regulatory Toxicology and Pharmacology*, vol. 52, pp. 46-52, 2008.

Scheuplein, "Site Variations in Diffusion and Permeability," *The Physiology and Pathophysiology of the Skin*, (Jarrett, A., ed.), Academic Press, pp. 1731-1752, 1978.

Feldmann et al., "Regional Variation in Percutaneous Penetration of $^{14}C$ Cortisol in Man," *The Journal of Investigative Dermatology*, vol. 48, No. 2, pp. 181-183, 1967.

Maibach et al., "Regional Variation in Percutaneous Penetration in Man," *Arch. Environ. Health*, vol. 23, pp. 208-211, Sep. 1971.

Watkinson et al., "Reduced barrier efficiency in axillary stratum corneum," *International Journal of Cosmetic Science*, vol. 24, pp. 151-161, 2002.

Bals-Pratsch et al., "Transdermal Testosterone Substitution Therapy for Male Hypogonadism," *Lancet*, vol. 118, No. 1, pp. 943-946, 1986.

Wang et al, "Pharmacokinetics of Transdermal Testosterone Gel in Hypogonadal Men: Application of Gel at One Site *Versus* Four Sites: A General Clinical Research Center Study," *The Journal of Clinical Endocrinology & Metabolism*, vol. 85, No. 3, pp. 964-969, 2000.

Steidle et al., "AA2500 Testosterone Gel Normalizes Androgen Levels in Aging Males with Improvements in Body Composition and Sexual Function," *The Journal of Endocrinology & Metabolism*, vol. 88, No. 6, pp. 2673-2682, 2003.

Foote, "The hydraulic influence in androgen-related hair growth: implications in autoimmune disease," *Medical Hypotheses*, vol. 59, No. 5, pp. 522-526, 2002.

Long et al., "Antiandrogenic Effects of Novel Androgen Synthesis Inhibitors on Hormone-dependent Prostate Cancer," *Cancer Research*, vol. 60, pp. 6630-6640, Dec. 1, 2000.

Zhu et al., "Androgen-Induced Prostate-Specific Antigen Gene Expression is Mediated via Dihydrotestosterone in LNCaP Cells," *Journal of Andrology*, vol. 24, No. 5, Sep./Oct. 2003.

Takayasu et al., "Activity of Testosterone 5α-Reductase in Various Tissues of Human Skin," *The Journal of Investigative Dermatology*, vol. 74, pp. 187-191, 1980.

Wilson et al., "The Conversion of Testosterone to 5α-Androstan-1β-o1-3-one (Dihydrotestosterone) by Skin Slices of Man," *The Journal of Clinical Investigation*, vol. 48, pp. 371-379, 1969.

Tenover, "The Androgen-Deficient Aging Male: Current Treatment Options," *Reviews in Urology*, vol. 5, Suppl. 1, pp. S22-S28, 2003.

McClure et al., "Hypogonadal Impotence Treated by Transdermal Testosterone," *Urology*, vol. 37, No. 3, pp. 224-228, 1991.

Findlay et al., "Treatment of Primary Hypogonadism in Men by the Transdermal Administration of Testosterone," *J. Clinc. Endocrinol. Metab.*, vol. 68, Suppl. 2, pp. 369-373, 1989.

Wang et al., "Long-Term Testosterone Gel (AndroGel) Treatment Maintains Beneficial Effects on Sexual Function and Mood, Lean and Fat Mass, and Bone Mineral Density in Hypogonadal Men," *The Journal of Endocrinology & Metabolism*, vol. 89, No. 5, pp. 2085-2098, 2004.

Chew et al., "Transdermal Drug Delivery: Influence of Anatomical Site," *Encyclopedia of Pharmaceutical Technology*, Marcel Dekker, pp. 1-15, 2005.

Bernard et al., "Expression of type 1 5α-reductase and metabolism of testosterone in reconstructed human epidermis (SkinEthic®): a new model for screening skin-targeted androgen modulators," *International Journal of Cosmetic Science*, vol. 22, pp. 397-407, 2000.

Office Action issued on May 26, 2010 by the Examiner in U.S. Appl. No. 11/978,556 (US2008/0131494).

Office Action issued on Jan. 7, 2010 by the Examiner in U.S. Appl. No. 11/905,926 (US 2008/0152597).

Bhatt, P. P. "Finite Dose Transport of Drugs in Liquid Formulations Through Stratum Corneum: Analytical Solution to a Diffusion Model", *International Journal of Pharmaceutics*, Elsevier Science Publishers B.V., Amsterdam, vol. 50, pp. 197-203 (1989).

Bucks, Percutaneous Absorption of Hydroquinone in Humans: Effect of 1-Dodecylazacycloheptan-2-One (Azone) and the 2-Ethylhexyl Ester of 4-(Dimethylamino) Benzoic Acid (Escalol 507), *Journal of Toxicology and Evironmental Health*, vol. 24, pp. 279-289 (1988).

Coldman, M.F., "Enhancement of Percutaneous Absorption by the Use of Volatile: Nonvolatile Systems and Vehicles," *Journal of Pharmaceutical Sciences*, vol. 58, No. 9, pp. 1098-1102 (1969).

(56) References Cited

OTHER PUBLICATIONS

Feldman, R.J., "Percutaneous Penetration of 14C Hydrocortisone in Man," *Arch. Derm.*, vol. 94, pp. 649-651 (1966).
Fraser et al., "An Initial Pharmacokinetic Study with a Metered Dose Transdermal System for Delivery of the Progestogen Nestrone as a Possible Future Contraceptive," *Contraception*, 76:432-438 (2007).
Good et al., "A New Transdermal Delivery System for Estraiol," *Journal of Controlled Release* 2:89-97 (1985).
Leichtnam et al., "Identification of Penetration Enhancers for Testosterone Transdermal Delivery from Spray Formulations", *Journal of Controlled Release*, 113:57-62 (2006).
Physicians' Desk Reference (49Ed.), Medical Economics Company, Inc., Montvale, N.J., "Tensilon®" pp. 1151-1152 (1995).
Thomas et al., "The Transdermal Revolution," *Drug Discovery Today (DDT)*, 9(16):697-703 (2004).
Confrancesco et al., "Transdermal Testosterone Delivery Systems," The Endocrinologist, vol. 6, No. 3, pp. 207-213.
Armory et al., "The therapeutic potential of testosterone patches," Exp. Opin. Invest. Drugs, vol. 7, No. 11, pp. 1977-1985, 1998.
Groscurth, "Anatomy of Sweat Glands," Hyperhidrosis and Botulinum Toxin in Dermatology, vol. 30, pp. 1-9, 2002.
Saga, "Structure and Function of Human Sweat Glands Studied with Histochemistry and Cytochemistry," Prog. in Histochem. And Cytochem., vol. 37, pp. 323-386, 2002.
Shimizu, Shimizu's Textbook of Dermatology, pp. 23-25, Hokkaido University Press, Japan, 2007.
Berti et al., "Transcutaneous drug delivery: a practical review," Mayo Clin. Proc., vol. 70, No. 6, pp. 581-586, Jun. 1995.
Solvay Pharmaceuticals, "AndroGel® testosterone gel," prescribing information, Sep. 2009.
Solvay Pharmaceuticals, "AndroGel® testosterone gel," medication guide, Sep. 2009.
Auxilium Pharmacuticals, "Testim® testosterone gel," prescribing information, Sep. 2009.
Auxilium Pharmacuticals, "Testim® testosterone gel," medication guide, Sep. 2009.
Nicolazzo et al., "Synergistic enhancement of testosterone transdermal delivery," Journal of Controlled Release, vol. 103, pp. 577-585, 2005.
Office Action issued on Jan. 18, 2012 by the Examiner in U.S. Appl. No. 12/642,301 (US 2010/0166674).
European Search Report issued on Jan. 20, 2012 for application No. EP 06741180 (corresponding to US 2006/0280783).
A.S. Albrieux et al., "The Local Action of Testosterone Propionate on the Development of Axillary Hair in Man", Journal of Clinical Endocrinology, 1949, vol. 9, No. 12, pp. 1434-1436.
E. Ben-Galim et al., "Topically Applied Testosterone and Phallic Growth. Its Effects in Male Children With Hypopituitarism and Microphallus", American Journal of Disease and Children (1960), (1980), vol. 134, pp. 296-298.
Office Action issued on Oct. 13, 2010 by the Examiner in U.S. Appl. No. 11/905,926 (US 2008/0152597).
Office Action issued on Mar. 30, 2011 by the Examiner in U.S. Appl. No. 11/905,926 (US 2008/0152597).
Cutter, "Compounded Percutaneous Testosterone Gel: Use and Effects in Hypogonadal Men," JABFP, vol. 14, No, 1, pp. 22-32, Feb. 2001.
Jones, "The History of Pluronic Lechitin Organogel: An Interview with Marty Jones, BS Pharm., FACA, FIACP," International Journal of Pharmaceutical Compounding, vol. 7, No. 3, pp. 1801-182, May/Jun. 2003.
Office Action issued on Jun. 27, 2011 by the Examiner in U.S. Appl. No. 11/445,463 (US 2006/0280783).
Yu et al., "Sexual Development in a Two-Year Old Boy Induced by Topical Exposure to Testosterone," Pediatrics, vol. 104;e23, pp. 1-2, Aug. 2, 1999.

Papa, "Effect of Topical Hormones on Aging Human Skin," J. Soc. Cosmetic Chemists, vol. 18, pp. 549-562, Aug. 19, 1967.
Hancock et al., "Characteristics and Significance of the Amorphous State in Pharmaceutical Systems," J. Pharmaceut. Sci., vol. 86, pp. 1-12, Jan. 1997.
Lipp, "Selection and Use of Crystallization Inhibitors for Matrix-Type Transdermal Drug-delivery Systems Containing Sex Steroids," J. Pharm. Pharmacol., vol. 50, pp. 1343-1349, Dec. 1998.
Notice of Allowance issued on Feb. 12, 2013 by the Examiner in U.S. Appl. No. 11/445,463 (U.S. Pat. No. 8,435,944).
Office Action issued on Jun. 20, 2012 by the Examiner in U.S. Appl. No. 11/445,463 (U.S. Pat. No. 8,435,944).
Non-Final Office Action issued Dec. 18, 2008, in U.S. Appl. No. 11/513,342 (US 2007/0071803).
Non-Final Office Action issued Aug. 8, 2008, in U.S. Appl. No. 11/019,542 (US 2005/0181032).
Non-Final Office Action issued Jan. 28, 2009, in U.S. Appl. No. 11/019,121 (US 2005/0186141).
Non-Final Office Action issued Jul. 14, 2008, in U.S. Appl. No. 10/870,546 (US 2005/0002868).
International Search Report from PCT/AU03/00784 dated Aug. 28, 2003 (corresponding to US 2005/0186141).
International Search Report from PCT/AU03/00785 dated Aug. 29, 2003 (corresponding to US 2005/0181032).
Wester et al., "Regional Variation in Percutaneous Absorption," Percutaneous Absorption Drugs-Cosmetics-Mechanisms-Methodology, 3$^{rd}$ Ed., 1999, pp. 107-116.
Chew et al., "Transdermal Drug Delivery: Influence of Anatomical Site," *Encyclopedia of Pharmaceutical Technology*, 2005, pp. 1-15.
Office Action issued on Jul. 24, 2008 by the Examiner in U.S. Appl. No. 11/445,463 (US 2006/0280783).
Office Action issued on Mar. 19, 2009 by the Examiner in U.S. Appl. No. 11/445,463 (US 2006/0280783).
Office Action issued on Mar. 8, 2010 by the Examiner in U.S. Appl. No. 11/445,463 (US 2006/0280783).
Office Action issued on Sep. 1, 2011 in U.S. Appl. No. 12/823,448 (US 2010/0322884).
Office Action issued on Aug. 1, 2012 in U.S. Appl. No. 12/823,448 (US 2010/0322884).
Office Action issued on Mar. 18, 2013 in U.S. Appl. No. 12/823,448 (US 2010/0322884).
Notice of Allowance issued on May 13, 2013 in U.S. Appl. No. 12/823,448 (US 2010/0322884).
Office Action issued on Oct. 31, 2013 in U.S. Appl. No. 12/823,448 (US 2010/0322884).
Notice of Allowance issued on Jul. 16, 2014 in U.S. Appl. No. 12/823,448 (US 2010/0322884).
Notice of Allowance issued on Nov. 26, 2014 in U.S. Appl. No. 12/823,448 (US 2010/0322884).
Chien, "Transdermal Controlled-Release Drug Administration," Novel Drug Delivery Systems, Chapter 5, pp. 149-217, Marcel Dekker, Inc., 1982.
Finnin et al., Enhancement of Epidermal Penetration of NSAIDS by Padimate O, Octyl Salicylate and Octyl Methoxycinnamate, Pharm. Res., vol. 14, p. S-304, Nov. 1997, Abstract.
Pfister, "Transdermal and Dermal Therapeutic Systems: Current Status," Transdermal and Topical Drug Delivery Systems, Chapter 2, pp. 33-112, 1997.
Lee et al., "The Role of Corticosteroids in Dermatology," Aust. Prescr., vol. 21, pp. 9-11, Jan. 1998.
Wang et al., "Transdermal Testosterone Gel Improves Sexual Function, Mood, Muscle Strength, and Body Composition Parameters in Hypogonadal Men," J. Clin. Endocrinology & Metabolism, vol. 85. pp. 2839-2853, Aug. 2000.
Swerdloff et al., "Long-Term Pharmacokinetics of Transdermal Testosterone Gel in Hypogonadal Men," J. Clin. Endocrinology & Metabolism, vol. 85, pp. 4500-4510, Dec. 2000.

METHOD AND COMPOSITION FOR TRANSDERMAL DRUG DELIVERY

FIELD OF THE INVENTION

The present invention relates to a method and composition for transdermal delivery of a physiologically active agent. It has particular but not exclusive application to the delivery of an agent in areas prone to perspiration.

BACKGROUND OF THE INVENTION

Efficient transdermal delivery of a physiologically active agent offers several clinical and patient advantages in treatment of disease.

Drug delivery by injection is traditionally the quickest route of administration to the systemic circulation, however the duration of action of is often short lived and the mode of delivery is invasive and painful. Transdermal drug delivery is receiving increased attention due to the ability of the administration regime to provide a controlled route for the release of an active agent to the systemic circulation.

However, transdermal drug delivery is complicated by the fact that the skin behaves as a natural barrier. As a result, the success of transdermal delivery system often relies on the ability of a composition to be able to penetrate the stratum corneum of the skin and thereby transport an active agent across the skin.

Problems with transdermal delivery arise particularly in cases where a drug is slow to be absorbed through the skin or where a relative high dose of drug needs to be absorbed. In these circumstances it is often necessary to apply a transdermal composition to a large area of skin in order to achieve the required dose.

One example of this problem is encountered in the administration of androgens such as testosterone. Recent estimates show that approximately 13 million men in the United States experience testosterone deficiency and less than 10% receive treatment for the condition. The daily dose required to maintain testosterone levels within the normal range is relatively high (typically 5-10 mg/day), thus it provides a challenge for transdermal delivery. Similar problems occur with progesterone. The previously used topical administration of testosterone, for example in treatment of hypogonadism, requires application of gel or cream to a wide area of the body and that the area of application remains covered. Application of composition over a wide area severely increases the risk of transfer from patient to partner or child, thus persons such as family members may be subjected to accidental dosing of the drug. This can have serious consequences.

Transdermal administration of some drugs may also be accompanied by undesirable side effects. For example, testosterone is responsible for increasing perspiration and producing perspiration related odour in the presence of the enzyme 5-alpha-reductase which converts testosterone to dihydrotestosterone (DHT). Scrotal skin has a relatively high level of 5-alpha-reductase and continuous trans-scrotal delivery of testosterone produces levels of DHT and DHT/testosterone ratios 4 to 5 fold greater than normal. Such abnormal levels and ratios may give rise to undesirable side effects.

Problems also arise with the location of application, and side effects associated with the location. Ahmed, S. R., et al. (J Clin Endocrinol Metab (1988) 66:546-557) and Findlay, J. C. (J Clin Endocrinol Metab (1989) 68:369-373) report that the 60 $cm^2$ ALZA trans-scrotal system delivers about 3.7 mg/day and produces low-normal testosterone levels in hypogonadal men. Such dosages are believed to be somewhat less than the amount needed to mimic endogenous production (5-10 mg/day).

Trans-scrotal delivery of testosterone is also associated with high dihydrotestosterone (DHT) and DHT/testosterone ratio levels and does not provide a level of testosterone delivery that mimics endogenous production. Further, scrotal skin is sensitive and as noted above, limited in area, which may result in discomfort and poor patient acceptance of this modality of delivery.

Many transdermal compositions utilise penetration enhancers to assist delivery of the pharmaceutical active across the skin. Increased cutaneous blood flow and subsequent heat production is also reported to assist. U.S. Pat. No. 6,743,448 describes a topical testosterone formulation comprising arginine which is said to facilitate the production of nitrous oxide and enhance vasodilation.

However locally induced vasodilation and subsequent heating, particularly in areas having increased cutaneous blood flow such as the axilla is likely to cause excess perspiration and discomfort, due to the increased number of sweat glands present in such areas. This can be problematic for the subject on the basis that transdermal delivery of some pharmaceutical actives may be hindered by the use of antiperspirants and/or deodorants. This is undesirable because delivery may be compromised because of perspiration, resulting in inconsistent delivery and/or patient acceptability and compliance is hindered by instructions not to use antiperspirant or deodorant with drug delivery that promotes perspiration.

There is therefore a need for a method and composition for transdermal administration which provides rapid, consistent delivery and allows the area of application to be minimised, as well as being convenient for subjects to use desirably with reduced side effects to subjects and others with whom they come in contact.

SUMMARY OF THE INVENTION

In accordance with one aspect, the invention provides a transdermal drug delivery composition which includes (i) at least one physiologically active agent; and (ii) at least one volatile solvent; and (iii) at least one viscosity modulating agent. In some embodiments, the composition further comprises a penetration enhancer. In some embodiments, the viscosity modulating agent is a gelling or thickening agent. In some embodiments, the solvent is a lower alkyl alcohol or a mixture of such alcohols. In some embodiments, the penetration enhancer is one or a mixture of octyl dimethyl-para-aminobenzoate, octyl para-methoxycinnamate and octisalate. In some embodiments, the composition further comprises an antiperspirant and/or a deodorant.

In accordance with another aspect, the invention provides a method of delivering an active agent systemically to a patient by application of the active agent to one or more axilla. In some embodiments, administration is essentially only to the axilla. In some embodiments, an antiperspirant and/or a deodorant is applied at about the same time as a composition comprising the active agent.

In accordance with another aspect, the invention provides a method of treatment of testosterone deficiency of a subject comprising delivery of an androgenic compound according to the method describe above, in which the active agent is the androgenic compound.

In accordance with another aspect, the invention provides a method of delivering an agent systemically to a patient by application of the active agent with a volatile solvent to one or more axilla. In some embodiments, the active agent is in a transdermal drug delivery composition as described above.

In accordance with another aspect, the invention provides a method of transdermal testosterone delivery to a subject comprising topically applying to an area of skin of a subject a transdermal composition comprising (i) an androgenic compound; and (ii) a volatile carrier; and (iii) at least one dermal penetration enhancer; and (iv) at least one viscosity modulating agent. In some embodiments, the androgenic compound is testosterone or a derivative thereof. In some embodiments, the area of skin is the axilla and testosterone is delivered resulting in a blood level of at least a predetermined amount.

DETAILED DESCRIPTION

Figure 1:
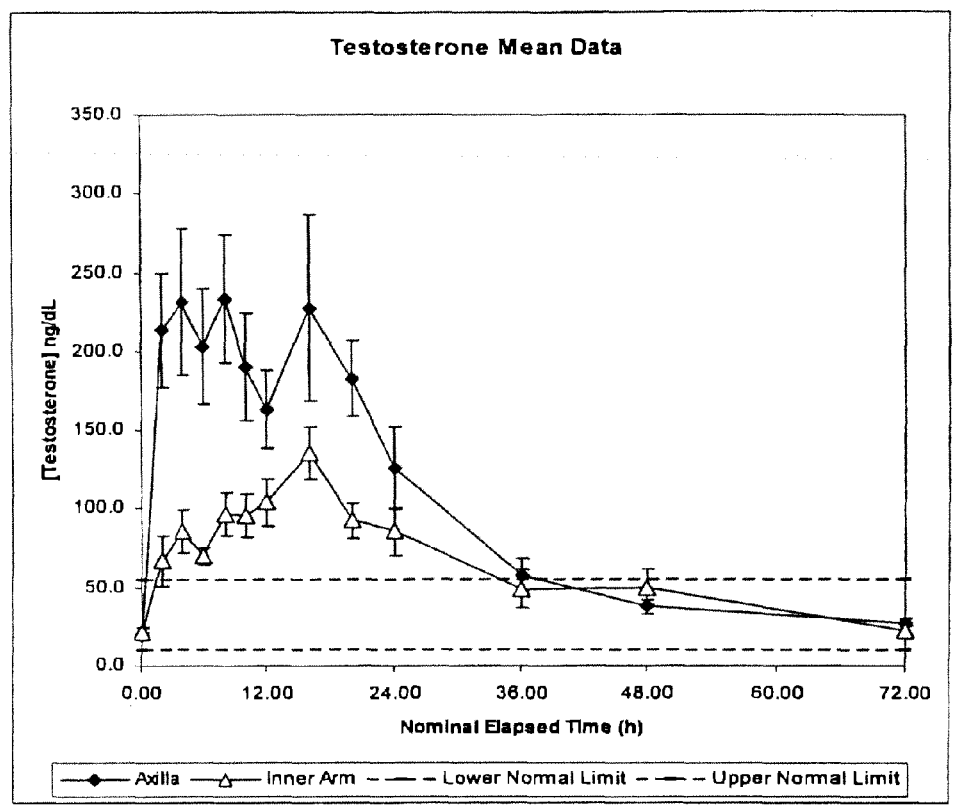
FIG. 1 is a graph showing the variation in blood level of testosterone with time after transdermal application.

The applicant has developed a method and a composition for transdermal administration which allows rapid delivery of active agents and reduces the risk of undesirable side effects in a patient. The delivery is "rapid" in the sense that little time of the patient is required. For example, in one embodiment, the transdermal composition is dry within 3 minutes. Pharmacodynamically, delivery of the active is substantially "steady-state", once a reservoir of the active is established in the skin. The reservoir is maintained (ie, "topped-up") by daily doses of the composition. Steady-state is the practical description of the delivery profile—there is some, but surprisingly minor, variation in delivery rates between doses. The invention therefore provides a method of administration which allows rapid delivery of active agents and minimises the risk of side effects in a patient.

The applicant has surprisingly observed that the transdermal composition of the current invention has antiperspirant and/or deodorant properties. The composition therefore allows the active agent to be rapidly delivered whilst also enabling perspiration and/or odour to be reduced. The use of the invention thus permits use of areas such as the axilla for transdermal drug delivery without patient inconvenience of not using normal antiperspirant/deodorant products (important for patient compliance) which may otherwise interfere with delivery of the active.

As such, there is provided a transdermal drug delivery composition which includes at least one physiologically active agent; and at least one volatile solvent; and at least one viscosity modulating agent. Preferably the viscosity modulating agent is a gelling or thickening agent. The viscosity modulating agent may be a thickening agent and suitable thickening agents include polyvinyl pyrrolidone. In some embodiments, the thickening agent is an antiperspirant or the composition further includes an antiperspirant and/or a deodorant.

In this specification and the claims, the term "viscosity modulating agent" is used to refer to a component of the composition which alters the viscosity of the overall resulting composition. The nature of the viscosity modulating agent depends not only on the agent itself, but also the proportion in which it is present and the presence or absence of other components. For example, a gelling agent may act as a viscosity modulating agent providing that an activator for that gelling agent is present. For example, hydroxypropylmethylcellulose (HPMC) may be used in a composition with an activator, in which the volatile solvent is a lower alkyl alcohol at a concentration of around 2% w/w. A suitable activator would be sodium chloride. Concentration may be important as, in this example, at 0.1% w/w HPMC has different effects. A thickening agent is one which increases viscosity, and is often anhydrous. Viscosity modulating agents are further described below.

Further, the term "transdermal" is used co-terminously with "topical" in describing the application of agents to the skin. Both terms "topical" and "transdermal" are used herein in the broadest sense to refer to administration of a drug to the skin surface of an animal, including humans, so that the drug passes through the skin tissue. Unless otherwise stated or implied, the terms topical drug delivery and transdermal drug delivery are used interchangeably. From a strict drug-delivery perspective, "transdermal" is sometimes used to refer only to systemic delivery through the skin whereas "topical" requires only delivery into or on the skin for local effect. The invention described in this specification is equally applicable to both transdermal and topical modes of delivery, and is described here as "transdermal" only for convenience. For avoidance of doubt, the invention provides in various embodiments compositions and methods suitable for topical application corresponding to those described in the specification as transdermal applications.

Typically, the composition appears like a lotion. In this context, "lotion" is used in its broad descriptive sense, rather than the more specific formulatory sense which refers to a mixed phase or suspension of active. The composition of the invention is often a true solution, but with increased viscosity so that its viscosity is more similar to that usually associated with a lotion. The viscosity of the composition is preferably greater than that of water but less than about 300 centipoise. The viscosity in different embodiments is in the range of 10 to 200, 20 to 100 or 30 to 50 centipoise.

In another embodiment, there is provided a transdermal drug delivery composition which includes at least one physiologically active, at least one volatile solvent, and at least one viscosity modulating agent and without a penetration enhancer.

In a different embodiment, there is provided a transdermal drug delivery composition which includes at least one physiologically active agent, at least one volatile solvent, at least one viscosity modulating agent, and at least one penetration enhancer. The penetration enhancer assists in the uptake of the physiologically active agent at least through the outer layers of the skin, typically to form a reservoir of active within the skin. Typical penetration enhancers suitable for use in the invention are further described below.

The volatile solvent (also sometimes called a "volatile carrier" or "vehicle") will typically be present in a higher concentration, such as 80% or more w/w. The volatile solvent may be any such solvent that is pharmacologically suitable and many such solvents are known in the art. One of the advantages of the inclusion of a volatile solvent or volatile carrier is that it facilitates the composition to dry rapidly, allow the absorption of the active agent, and avoid the problems of accidentally dosing others by confining administration to a small area of skin, preferably the axilla. Preferably the volatile solvent has a vapour pressure above 35 mm Hg at atmospheric pressure and normal skin temperature of 32 degrees Celsius.

Preferably, the solvent is a lower alkyl alcohol or a mixture of such alcohols. Suitable solvents include ethanol, ethyl acetate, isopropanol, acetone, ethyl formate, methyl acetate, methyl ethyl ketone, pentane and chloroform or mixture thereof in the range of about 40 to 99% v/v of the composition, preferably more than 50%, 60%, 70% or 80%. An aerosol propellant, such as dimethyl ether or R134a, may also constitute a volatile solvent for the purpose of the present invention.

Preferably the compositions of the invention are non-occlusive, in that in the broadest sense, the composition is not trapped to the skin, or the skin is not closed to the atmosphere, by means of a patch device, fixed reservoir, application chamber, tape, bandage, sticking plaster, or the like, which remains on the skin a the site of application for a prolonged length of term. Such devices tend to be uncomfortable for the wearer or can be embarrassing or unsightly.

The viscosity modulating agent will commonly be a thickening agent or a gelling agent. It will often be used to increase the viscosity of the composition containing a solution of the physiologically active agent in the volatile solvent. Given the nature of the volatile solvents, the solution will typically have very low viscosity. The purpose of the viscosity modulating agent is to increase the viscosity of the solution such that the composition is retained in the vicinity of the area of application for a brief period of time so as to permit increased uptake of the physiologically active agent at that site. The viscosity modulating agent will typically increase the viscosity to about that of a typical lotion (eg, sunscreen), but not to the point where the composition becomes a gel. Typically, the viscosity of a transdermal drug delivery composition according to the invention will be less than 300 centipoise and often about 150 centipoise.

The viscosity modulating agent must retain its activity in the context of the other components of the composition of the invention. In particular, the thickening agent must remain active and stable in this environment. For example, where the composition has a high alcohol content (for example, where the volatile solvent comprises primarily alcohol at greater than 80% v/v), the thickening agent must be effective in a high alcoholic environment. Having these requirements in mind, a skilled person can select several thickening agents from those known in the art. Desirably, a thickening agent also inhibits the solvent evaporation rate so as to enhance the so-called "solvent burst" of active agent into the skin at the site of application.

It will be appreciated by one skilled in the art that the amount of thickening agent required is a question of degree and compromise with other parameters. It is also known that many thickening agents have peak activity at a particular concentration, and that activity may drop off substantially with slightly higher and slightly lower percentage concentrations. For example, in one preferred embodiment where the composition comprises over 80% alcohol and the thickening agent used is PVP, the desirable concentration of PVP is between 1 and 3%, and its activity is substantially reduced outside that range.

Gelling agents are matrix-forming agents which, once activated, act by forming a matrix within and around the composition they are in. Thickening agents are usually anhydrous agents which increase the viscosity of the composition. In one embodiment, a thickening agent is used. The thickening agent may be an antiperspirant and/or an occlusive agent for the drug delivery composition. In another embodiment, both a deodorant and an antiperspirant are in a composition with the at least one active agent and dermal penetration enhancer. Suitable thickening agents include polyvinyl pyrrolidone or PVP (Povidone™). The antiperspirant may be an occlusive agent also, and a thickening, occlusive agent may have antiperspirant effects.

Despite the inherent antiperspirant and/or deodorant properties of the compositions of the invention, the composition may be optionally administered with deodorant and antiperspirant additives that do not interfere with the active. In another form, there is provided a transdermal drug delivery composition which includes at least one physiologically active agent; and at least one volatile solvent; and at least one antiperspirant or deodorant.

The antiperspirant agent may be any suitable substance that reduces or inhibits the production of perspiration. In some instances, an antiperspirant agent can also provide deodorant benefits. Preferably, the antiperspirant agent is selected from the group consisting of inorganic or organic salts of aluminium, zirconium, zinc or mixtures thereof.

In one embodiment, the antiperspirant agent is an aluminium salt having the general formula:

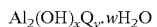

where Q is chlorine, bromine or iodine;
x is 2 to 5;
x+y=6, where x and y do not need to be integers; and
wH$_2$O represents a variable amount of hydration.

In another embodiment, the antiperspirant agent is a zirconium salt of the following general formula:

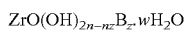

where
z is a variable in the range of from 0.9 to 2.0 so that the value of 2n−nz is zero or a positive;
n is the valency of B;
B is selected from the group consisting of chloride, other halide, sulphamate, sulphate and mixtures thereof; and
wH$_2$O represents a variable amount of hydration.

In a preferred embodiment, the antiperspirant agent is selected from the group consisting of aluminium chloride, aluminium chlorohydrate, aluminium chlorohydrex polyethylene glycol, aluminium chlorohydrex propylene glycol, aluminium dichlorohydrate, aluminium dichlorohydrex polyethylene glycol, aluminium dichlorohydrex propylene glycol, aluminium sesquichlorohydrate, aluminium sesquichlorohydrex polyethylene glycol, aluminium sesquichlorohydrex propylene glycol, aluminium zirconium octachlorohydrate, aluminium zirconium octachlorohydrex gly, aluminium zirconium pentachlorohydrate, aluminium zirconium pentachlorohydrex gly, aluminium zirconium tetrachlorohydrate, aluminium zirconium tetrachlorohydrex gly, aluminium zirconium trichlorohydrate and aluminium zirconium trichlorohydrex gly. These antiperspirant agents have approved listings under the United States Food & Drug Administration Federal Register.

The present invention also contemplates that other antiperspirant agents may also be used. Examples of these antiperspirant agents include aluminium bromohydrate, aluminium chloride, aluminium citrate, aluminium sulfate, ammonium alum, cobalt acetylmethionate, potassium alum, sodium alum and sodium aluminium chlorohydroxy lactate.

In another embodiment, the composition of the invention comprises a deodorant agent. The deodorant agent may be any suitable substance that provides deodorancy benefits in masking or neutralising odours that are produced by the action of bacteria. Generally, deodorant agents do not interfere with the production of perspiration. Representative examples of deodorant agents include, but are not limited to, one or more of cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmithyl sarcosine, lauroyl satcosine, N-myristoyl glycine, potassium N-lauryl sarcosine, stearyl, trimethyl ammonium chloride, sodium aluminium chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odour absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

In a preferred embodiment, the composition comprises a combination of antiperspirant and deodorant agents.

The antiperspirant and deodorant agents may be present in the composition in any amount that provides beneficial antiperspirant and/or deodorancy effects. The antiperspirant agent or deodorant agent may be present in an amount of from about 0.05 to 60%, and is preferably from about 1 to 40%, more preferably from about 5 to 30% and even more preferably from about 8 to 15% by weight of the composition. Where the composition of the invention comprises a combination of antiperspirant and deodorant agents, the combined amounts of these agents is preferably within the preferred range stated above.

The composition may be applied to any area of skin. Preferably it is applied to areas of skin having increased cutaneous blood flow, such as the axilla, scrotum, between toes, groin, plantar arch of the foot or palm of the hand. Other suitable areas include where there is suitably permeable skin. In particularly, it is desirable to apply it to only one or more of these areas while still effectively delivering the required dose of active agent. It is also known that some areas of the skin are relatively more permeable to active agents than others. The invention is usefully employed to deliver active agent through these areas only, thus limiting the total area of skin to which the composition must be applied in order to deliver an effective dose of the active agent.

Moreover, the invention provides a method for transdermal delivery of an active agent to areas of the skin prone to perspiration, particularly higher rates of perspiration relative to other areas. Such areas of skin have typically not been preferred for transdermal delivery because of the desirability for patients to be able to maintain use of antiperspirants and deodorants. In a preferred form, the method provides for administration of a composition including the active agent to those areas of skin which provide maximal systemic absorption. It is believed that this is due, at least in part, to increased cutaneous blood flow and heat. These areas may be one of more of the axilla, scrotum, groin, planter arch of foot, palm of hand or forehead. Preferably the area is at least one axilla. These areas in particular may benefit greatly from the antiperspirant and/or deodorant effects of the composition when it is applied.

In another form, the invention comprises a method of delivering an active agent systemically to a patient by application of the active agent to one or more axilla. The active agent is preferably in a transdermal drug delivery composition as described in this specification. Preferably, administration is essentially only to the axilla. In another form, administration is to areas selected from the group consisting of the axilla, scrotum, groin, planter arch of foot, palm of hand and forehead. In one form, the method avoids application or administration of the composition to the upper arms, shoulders or abdomen of a subject. The transdermal drug delivery composition of the present invention is capable, upon application to an area of skin, of delivering a therapeutically effective amount of active agent to the systemic circulation.

The composition may be applied to any area of skin on a subject, selected from one or more of planter foot arch, lateral ankle, palm, upper arm, ventral forearm, dorsal forearm, back, chest, thigh, abdomen, groin, scalp, axilla, forehead, lower back, buttocks or scrotum. The composition is preferably applied to those areas of skin which provide maximal systemic absorption due to increased cutaneous blood flow and heat. These areas may be one of more of the axilla, scrotum, planter arch of foot, palm of hand or forehead. Preferably the area is at least one axilla. These areas in particular may benefit greatly from the antiperspirant and/or deodorant effects of the composition when it is applied.

A further advantage of the compositions according to the invention is that a therapeutically effective amount may be applied to a minimal surface area, therefore minimising the unpleasant side effects and patient inconvenience associated with applying large amounts of a composition to a large surface area. Preferably the area of skin to which the composition is applied is less than 500 cm$^2$. Desirably, the area is less than 300 cm$^2$, 100 cm$^2$, 50 cm$^2$, 20 cm$^2$ 10 cm$^2$, and 5 cm$^2$.

A key advantage achievable with some embodiments of the invention is increased flux of the active, thereby enabling a greater proportion of active in a dose to be delivered to the patient and utilising a smaller area of skin. In some cases, a much smaller area than used to date is required, consequently improving patient acceptability and compliance. This is particularly applicable where the active otherwise has poor or low flux, a large systemic dose is desired and/or a faster onset of action is desired.

The penetration enhancer is also sometimes called an "absorption" enhancer. A number of penetration enhancers may be utilised including fatty acids, fatty acid esters, fatty alcohols, glycols and glycol esters, 1,3-dioxolanes and 1,3-dioxanes, macrocyclic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters and mixtures thereof. Most preferably the dermal penetration enhancer is selected from the list including oleic acid, oleyl alcohol, cyclopentadecanone (CPE-218™), sorbitan monooleate, glycerol monooleate, propylene glycol monolaurate, polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl dimethyl-para-aminobenzoate, octyl para-methoxycinnamate, octisalate and mixtures thereof.

Preferred penetration enhancers are sunscreen esters such as the compounds disclosed in our U.S. Pat. No. 6,299,900 the contents of which are herein incorporated by reference. These include the compounds being safe skin-tolerant ester sunscreens of formula:

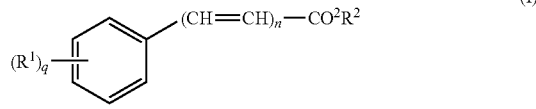

wherein $R^1$ is hydrogen, lower alkyl, lower alkoxy, halide, hydroxy or $NR^3R^4$;

$R^2$ is long chain alkyl;

$R^3$ and $R^4$ are each independently hydrogen, lower alkyl or $R^3$ and $R^4$ together with the nitrogen atom to which they are attached form a 5- or 6-membered heterocyclic ring;

n is 0 or 1; and q is 1 or 2.

Preferred penetration enhancers are esters having a long chain alkyl para-aminobenzoate, long chain alkyl dimethyl-para-aminobenzoate, long chain alkyl cinnamate, long chain alkyl methoxycinnamate or long chain alkyl salicylate; most preferably the penetration enhancer is one or a mixture of octyl dimethyl-para-aminobenzoate ("Padimate O"), octyl para-methoxycinnamate and octyl salicylate ("octisalate" per USP).

The concentration of absorption/penetration enhancer may be in the range from 10-10,000 weight percent of absorption/penetration enhancer based upon the weight of active ingredient. The ratio of penetration enhancer to active ingredient may vary considerably and will be governed as much as anything, by the pharmacological results that are required to be achieved. In principle, it is desirable that as little absorption enhancer as possible is used. However, usually the penetration enhancer is in the range from 0.01-15% of the total composition.

Heat can also act to enhance penetration of an active agent, together with or independently of such a penetration enhancer. Heat is not itself regarded as a "penetration enhancer". Without being bound by the theory or mode of action, it is believed that heat can disrupt and/or fluidise the lipid structures in the skin to enhance penetration. Accordingly, in one embodiment, the invention provides at least one physiologically active agent and at least one viscosity modulating agent which is applied in the presence of heat. Preferably, the composition also includes a dermal penetration enhancer.

Heat may result from utilising the patient's own body heat to warm the skin to the core body temperature (the outer layers of skin often being below that temperature) and/or the heat may be from an external source. Such external sources include conventional heat packs (eg, for therapeutic or physiotherapeutic uses), radiation heat (eg, heat lamps), exothermic chemical reactions or in situ generation of heat.

Heat is suggested to enhance the transdermal delivery of various drugs by increasing skin permeability, body fluid circulation, blood vessel wall permeability, rate-limiting membrane permeability, and drug solubility. Accordingly, whether or not heat is applied around the time of application of the composition, application of a transdermal composition is preferably to areas of skin having increased cutaneous blood flow, and therefore warmer. Such areas include but are not limited to, the planter arch of the foot, palm of the hand, axilla and scrotum. However associated with areas of increased heat is increased perspiration and perspiration related body odour. Therefore, it is desirable if the transdermal composition is also an antiperspirant and/or a deodorant. An antiperspirant reduces the amount of perspiration produced by blocking the sweat glands. A deodorant masks or covers the odour associated with perspiration, using either fragrance or an anti-bacterial ingredient to reduce odour-causing bacteria on the skin. Antiperspirants can have an indirect deodorant effect in the underarm area, but a deodorant cannot act as an antiperspirant. It is further desirable if known antiperspirants and/or deodorants can be added to the composition without inhibiting drug delivery.

Without being bound by any theory, the applicant believes that the viscosity modulating agent and/or penetration enhancer in the composition function to minimise perspiration, and that the volatile carrier functions to inhibit bacteria and therefore odour by a bactericidal activity of the carrier.

In one embodiment, the composition consists essentially of one physiologically active agent; one volatile solvent; and one viscosity modulating agent, each as described above. Preferably, it further includes a penetration enhancer as described above. In one embodiment, the viscosity modulating agent is an antiperspirant, and the composition optionally also includes a deodorant. Each of these embodiments may or may not also include water.

The invention also provides a use of at least one physiologically active agent; and at least one volatile solvent; and at least one viscosity modulating agent in the manufacture of a medicament for transdermal delivery of the active agent to a subject. The medicament is preferably for treatment or prevention of a condition treatable or preventable by the active.

In another embodiment of the invention, the composition may include at least one additional active agent and/or at least one additional inactive agent. In a different embodiment, the composition does not include a herbal extract (or like component), whether as a physiologically active agent or otherwise.

The transdermal drug delivery composition of the present invention is capable, upon application to an area of skin, of delivering a therapeutically effective amount of active agent to the systemic circulation. Accordingly, in one aspect, there is provided a method of transdermal delivery of an active agent comprising applying to an area of skin of a subject the transdermal composition described above. In particular, the method can be used to deliver a predetermined amount of active and/or sufficient active to achieve a predetermined bloodstream level or concentration of the active. For some actives (eg, those with a short half-life) other measures of the amount of active delivered will be appropriate.

The composition may also be administered by other known topical techniques including a lotion, gel, spray etc. These can be formulated by adding suitable carriers, excipients and thixotropic agents which are inert to the active to facilitate retaining the composition on the skin sufficiently for delivery of the active agent as contemplated by the invention.

The transdermal composition of the invention and the composition used in the method of the invention may be applied, including but not limited to axilla, of a subject in any of a range of forms. Suitable forms include for example lotions, gels, foams, pastes, soft solids, firm sticks, solutions, sprays, aerosols, roll-ons and the like, each of which represent different forms of the invention. The composition may be applied in an occlusive or non-occlusive manner. It is preferred that the composition is applied in a non-occlusive manner and in the most preferred embodiment the composition is applied as a lotion, aerosol or spray.

The transdermal composition of the invention and the composition used in the method of the invention may further comprise additional components that will facilitate its preparation into forms suitable for application to the axilla of a subject. Examples of additional components include but are not limited to surfactants, buffers, solvents and propellants.

It is particularly preferred that the composition of the invention and the composition used in the method of the invention is applied without being covered by adhesives, adhered patches, adhered bandages or films. Such devices tend to be uncomfortable for the wearer or can be embarrassing or unsightly. The invention allows non-occlusive administration of physiologically active agents by the transdermal compositions in the axilla under the subjects clothing.

In applying the composition of the invention, an antiperspirant and/or a deodorant may be applied at about the same time as the composition. Preferably, the antiperspirant and/or deodorant is applied after application of the composition of the invention. As noted above, in some embodiments of the invention, an antiperspirant and/or a deodorant may be incorporated within the composition, thus requiring only one substance to be applied by a patient. The antiperspirant and/or deodorant will be selected from those which do not interfere with the drug delivery mechanism. Preferably, the antiperspirant and deodorant added complement the natural antiperspirant and deodorising properties of the transdermal drug delivery composition itself as described above.

The invention also provides a method of transdermal drug delivery comprising applying a predetermined dose of a transdermal drug delivery composition as described above to a patient. As described below, a preferred form of the invention involves applying the composition to at least one axilla. In the composition of the invention, the invention extends to a method in which an antiperspirant and/or a deodorant is applied to the axilla region at about the same time as the transdermal drug delivery composition is applied. Preferably, the antiperspirant and/or deodorant is applied after the transdermal drug delivery composition is applied to at least one axilla region.

In the methods of the invention the compositions are preferably administered without being covered by an adhesive bandage, patch or other physical barrier bonded to the administration area. Preferably the transdermal composition becomes touch dry within three minutes of application to the area of skin, more preferably within about one minute.

The antiperspirant and/or deodorant properties of the composition are particularly advantageous when the physiologically active agent is testosterone or derivatives thereof for treating testosterone deficiency in a subject. Testosterone is responsible for increasing perspiration and producing perspiration and perspiration related odour in the presence of 5-alpha-reductase, due to the conversion of testosterone to dihydrotestosterone (DHT). Accordingly there is provided a composition as described above in which the physiologically active agent is selected from at least one or more of androgenic compound, such as testosterone or derivatives thereof. The physiologically active agent may therefore be selected from androgenic compounds which are synthetically derivatized from testosterone and are known to provide the same or a similar physiological activity. Such compounds include without limitation, testosterone salts, such as acetate, enanthate, cypionate, isobutyrate, dehydro-epiandrosterone, propionate, undecanoate esters and cyproterone acetate. In other embodiments, one or more of the following are included: 5-alpha-reductase inhibitors (such as finasteride, turosteride, LY-191704 and MK-386). Other suitable compounds include methyltestosterone, clostebol acetate, drostanolone, furazabol, nandrolone oxandrolone, stanozolol, trenbolone acetate, dihydro-testosterone, 17-.alpha.-methyl-19-nortestosterone and fluoxymesterone.

Contrary to what might be expected from the activity of testosterone, the applicant has found that testosterone may be administered in accordance with the invention to provide rapid delivery without inducing sweating and odour that distress a subject. The unacceptable levels of these side effects identified in the art have been attributed to the presence of elevated testosterone.

In a preferred embodiment of this aspect of the invention, the invention provides a method of treatment of testosterone deficiency in a subject comprising topically applying to an area of skin of a subject a transdermal composition comprising:

a physiologically active agent selected from at least one of testosterone or derivatives thereof;

a volatile carrier;

at least one dermal penetration enhancer; and at least one viscosity modulating agent.

In one embodiment, the carrier is isopropyl alcohol, the penetration enhancer is octisalate, the active agent is testosterone and the thickening agent is polyvinylpyrrolidone. These may be in the following percentages:

30% v/v carrier;

8% w/v enhancer;

1% w/v active;

2% w/v thickener;

10% v/v sterile water; and the balance ethanol.

In another embodiment, there is provided a transdermal drug delivery composition consisting essentially of the above 6 components in those proportions. In another form of the invention, these 6 components in these proportions are used in the manufacture of a medicament for the treatment of a subject, particular a subject in need of treatment with the active. For example, a subject suffering from decreased testosterone blood levels is treated with a composition where the active is testosterone or a related androgenic agent or testosterone derivative as set out above.

In further embodiments, the invention provides a method of treatment of oestrogen and/or progestin deficiency, a method of treatment of chronic pain, and a method of treatment of anxiety related disorders. Other actives as set-out below are also contemplated for use with the invention.

In one embodiment, a composition containing testosterone as the active agent is applied to the axilla of a patient to deliver testosterone resulting in a blood level of at least a predetermined amount. In one embodiment, the predetermined amount is the normal range. In the case of testosterone, the blood level achieved is at least 200 ng/dL, preferably 300-1000 ng/dL. Preferably, the composition is only applied to the axilla.

Physiologically active agents that may be used in the transdermal drug delivery compositions of the present invention include any locally or systemically active agents which are compatible with the penetration enhancers of the present invention and which can be delivered through the skin, particularly with the assistance of the dermal penetration enhancer to achieve a desired effect. These active agents are preferably therapeutics, and include (grouped by therapeutic class):

(a) Alimentary System agents including antidiarrhoeals such as diphenoxylate, loperamide and hyoscyamine.
(b) Cardiovascular System agents including:
  (i) antihypertensives such as hydralazine, minoxidil, captopril, enalapril, clonidine, prazosin, debrisoquine, diazoxide, guanethidine, methyldopa, reserpine, trimetaphan;
  (ii) Calcium channel blockers such as diltiazem, felodopine, amlodipine, nitrendipine, nifedipine and verapamil;
  (iii) antiarrhythmics such as amiodarone, flecainide, disopyramide, procainamide, mexiletene and quinidine;
  (iv) antiangina agents such as glyceryl trinitrate, erythritol tetranitrate, pentaerythritol tetranitrate, mannitol hexanitrate, perhexilene, isosorbide dinitrate and nicorandil;
  (v) beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;
  (vi) cardiotonic glycosides such as digoxin and other cardiac glycosides and theophylline derivatives;
  (vii) adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;
  (viii) vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol; and
  (ix) antimigraine preparations such as ergotamine, dihydroergotamine, methysergide, pizotifen and sumatriptan.
(c) Drugs Affecting Blood and Haemopoietic Tissues including:
  (i) Anticoagulants and thrombolytic agents such as warfarin, dicoumarol, low molecular weight heparins such as enoxaparin; streptokinase and its active derivatives; and
  (ii) haemostatic agents such as aprotinin, tranexamic acid and protamine.
(d) Drugs Affecting the Central Nervous System including:
  (i) Analgesics;
  (ii) antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine and dihydrocodeine; and
  (iii) Others include acetylsalicylic acid (aspirin), paracetamol, and phenazone.
(e) Hypnotics and sedatives such as the barbiturates, amylobarbitone, butobarbitone and pentobarbitone and other hypnotics and sedatives such as choral hydrate, chlormethiazole, hydroxyzine and meprobamate.
(f) Antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam.
(g) Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium.
(h) Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline.
(i) CNS stimulants such as caffeine.
(j) Anti-alzheimer's agents such as tacrine.
(k) Anti-parkinson agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923).
(l) Anticonvulsants such as phenyloin, valproic acid, primidone, phenobarbitone, methylphenobarbitone and carbamazepine, ethosuximide, methsuximide, phensuximide, sulthiame and clonazepam.
(m) Antiemetics, antinauseants such as the phenothiazines, prochioperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.
(n) Musculoskeletal System including:
  (i) Non-steroidal anti-inflammatory agents including their racemic mixtures or individual enantiomers where applicable, such, as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketoralac;
  (ii) Additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;
  (iii) Antirheumatoid agents such as penicillamine, aurothioglucose, sodium aurothiomalate, methotrexate and auranofin;
  (iv) Muscle relaxants such as baclofen, diazepam, cyclobenzaprine hydrochloride, dantrolene, methocarbamol, orphenadrine and quinine; and
  (v) Agents used in gout and hyperuricaemia such as allopurinol, colchicine, probenecid and sulphinpyrazone.
(o) Hormones and Steroids including:
  (i) Oestrogens such as oestradiol, oestriol, oestrone, ethinyloestradiol, mestranol, stilboestrol, dienoestrol, epioestriol, estropipate and zeranol;
  (ii) Progesterone and other progestagens such as allyloestrenol, dydrgesterone, lynoestrenol, norgestrel, norethyndrel, eclometrine, norethisterone, norethisterone acetate, gestodene, levonorgestrel, medroxyprogesterone and megestrol;

(iii) Antiandrogens such as cyproterone acetate and danazol;

(iv) Antioestrogens such as tamoxifen and epitiostanol and the aromatase inhibitors, exemestane and 4-hydroxyandrostenedione and its derivatives. Androgens and anabolic agents such as testosterone, methyltestosterone, clostebol acetate, drostanolone, furazabol, nandrolone oxandrolone, stanozolol, trenbolone acetate, dihydrotestosterone, 17-.alpha.-methyl-19-nortestosterone and fluoxymesterone;

(v) 5-alpha reductase inhibitors such as finasteride, turosteride, LY-191704 and MK-386;

(vi) Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide;

(vii) Further steroidal antiinflammatory agents such as cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, fluetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

(viii) Pituitary hormones and their active derivatives or analogs such as corticotrophin, thyrotropin, follicle stimulating hormone (FSH), luteinising hormone (LH) and gonadotrophin releasing hormone (GnRH);

(ix) Thyroid hormones such as calcitonin, thyroxine and liothyronine and antithyroid agents such as carbimazole and propylthiouracil; and (x) Other miscellaneous hormone agents such as octreotide.

(q) Pituitary inhibitors such as bromocriptine.

(r) Ovulation inducers such as clomiphene.

(s) Hypoglycaemic agents such as insulin, chlorpropamide, glibenclamide, gliclazide, glipizide, tolazamide, tolbutamide, rosiglitazone and metformin.

(t) Genitourinary System agents.

(u) Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene.

(v) Antidiuretics such as desmopressin, lypressin and vasopressin including their active derivatives or analogs.

(w) Obstetric drugs including agents acting on the uterus such as ergometrine, oxytocin and gemeprost.

(x) Prostaglandins such as alprostadil (PGE1), prostacyclin (PGI2), dinoprost (prostaglandin F2-alpha) and misoprostol.

(y) Antimicrobials including:

(i) cephalosporins such as cephalexin, cefoxytin and cephalothin;

(ii) penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin;

(iii) tetracyclines such as minocycline, chlortetracycline, tetracycline, demeclocycline, doxycycline, methacycline and oxytetracycline and other tetracycline-type antibiotics;

(iv) minoglycosides such as amikacin, gentamicin, kanamycin, neomycin, netilmicin and tobramycin. Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

(v) Quinolones such as nalidixic acid, cinoxacin, ciprofloxacin, enoxacin and norfloxacin. Sulphonamides such as phthalylsulphthiazole, sulfadoxine, sulphadiazine, sulphamethizole and sulphamethoxazole;

(vi) Sulphones such as dapsone; and (vii) Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide (z) Anti-tuberculosis drugs such as ethambutol, isoniazid, pyrazinamide, rifampicin and clofazimine. Antimalarials such as primaquine, pyrimethamine, chloroquine, hydroxychloroquine, quinine, mefloquine and halofantrine.

(aa) Antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine.

(ab) Anthelmintics such as mebendazole, thiabendazole, niclosamide, praziquantel, pyrantel embonate and diethylcarbamazine.

(ac) Cytotoxic agents such as plicamycin, cyclophosphamide, dacarbazine, fluorouracil and its prodrugs [described, for example, in International Journal of Pharmaceutics 111, 223-233 (1994)], methotrexate, procarbazine, 6-mercaptopurine and mucophenolic acid.

(ad) Metabolism agents including anorectic and weight reducing agents such as dexfenfluramine, fenfluramine, diethylpropion, mazindol and phentermine.

(ae) Agents used in hypercalcaemia such as calcitriol, dihydrotachysterol and their active derivatives or analogs.

(af) Respiratory System agents including:
- (i) antitussives such as ethylmorphine, dextromethorphan and pholcodine;
- (ii) expectorants such as acetylcysteine, bromhexine, emetine, guaiphenesin, ipecacuanha and saponins;
- (iii) decongestants such as phenylephrine, phenylpropanolamine and pseudoephedrine; and
- (iv) bronchospasm relaxants such as ephedrine, fenoterol, orciprenaline, rimiterol, salbutamol, tulobuterol, sodium cromoglycate, cromoglycic acid and its prodrugs [described, for example, in International Journal of Pharmaceutics 7, 63-75 (1980)], terbutaline, ipratropium bromide, salmeterol and theophylline and theophylline derivatives.

(ag) Allergy and Immune System agents including:
- (i) antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine.

(ah) Local anaesthetics such as bupivacaine, amethocaine, lignocaine, cinchocaine, dibucaine, mepivacaine, prilocaine and etidocaine.

(ai) Stratum corneum lipids, such as ceramides, cholesterol and free fatty acids, for improved skin barrier repair [Man, et al. J. Invest. Dermatol., 106(5), 1096, 1996].

(aj) Neuromuscular blocking agents such as suxamethonium, alcuronium, pancuronium, atracurium, gallamine, tubocurarine and vecuronium.

(ak) Smoking cessation agents such as nicotine, bupropion and ibogaine.

(al) Insecticides and other pesticides which are suitable for local or systemic application.

(am) Dermatological agents, such as vitamins A and E, vitamin E acetate and vitamin E sorbate.

(an) Allergens for desensitisation such as house dust mite allergen.

(ao) Nutritional agents, such as vitamins, essential amino acids and essential fats.

(ap) Keratolytics such as the alpha-hydroxy acids, glycollic acid and salicylic acid.

(aq) Psychicenergisers, such as 3-(2-aminopropyl)indole, 3-(2-aminobutyl)indole, and the like.

(ar) Anti-acne agents such as containing isotretinoin, tretinoin and benzoyl peroxide.

(as) Anti-psoriasis agents such as containing etretinate, cyclosporin and calcipotriol.

(at) Anti-itch agents such as capsaicin and its derivatives such as nonivamide [Tsai, et al. Drug. Dev. Ind. Pharm., 20(4), 719, 1994].

(au) Anticholinergic agents, which are effective for the inhibition of axillary sweating and for the control of prickly heat. The antiperspirant activity of agents such as methatropine nitrate, propantheline bromide, scopolamine, methscopolamine bromide, and the new class of soft antiperspirants, quaternary acyloxymethyl ammonium salts [described, for example, by Bodor et al, J. Med. chem. 23, 474 (1980) and also in United Kingdom Specification No. 2010270, published Jun. 27, 1979].

(av) Other physiologically active peptides and proteins, small to medium-sized peptides, e.g., vasopressin and human growth hormone.

Preferably the active agents are androgens, preferably testosterone; oestrogens, preferably estradiol; progesterone and other progestagens; broncho-dilators; antianxiety agents, preferably buspirone; and central nervous system agents, preferably fentanyl.

In another embodiment, the composition may further include a second active agent to provide the composition with additional usage benefits. The second active agent may be any one of those listed above, or herbal extracts and/or cosmetic agents (such as, age spot and keratose removing agents, anti-aging agents, antioxidants, and hydroxy acids).

Preferably the second active agent is an antifungal agent. Fungal infections are common in areas of the body having higher production of heat and perspiration.

In yet another embodiment, the composition may further comprise one or more inactive agents. Such inactive ingredients may be referred to as "additives". Examples of such additives include but are not limited to, humectants, deodorant agents, antiperspirants, pH adjusting agents, preservatives, emulsifiers, occlusive agents (including without limitation patches and film formers), solubilizing agents, colorants, and surfactants (including without limitation anionic surfactants).

The method of the invention is particularly suited to treatment of testosterone insufficiency and the conditions and diseases associated therewith.

The invention may be applied to a range of active agents and in the treatment of a range of conditions. These include the delivery of oestradiol, progestin, ADHD agents and fentanyl, which may be used to treat various indications as already known by treatment through other routes of administration.

The preferred method of the invention wherein the active agent is testosterone or a derivative thereof, may be used to treat testosterone deficiency in men and women and the conditions and diseases resulting therefrom. The composition may comprise testosterone or a derivative thereof. There are number of closely related androgenic compounds which are synthetically derivatized from testosterone are known to provide the same or a similar physiologic activity, as discussed above.

Testosterone production in both men and women declines naturally with age. Testosterone deficiency may result from disease or damage to the hypothalamus, pituitary gland, or testicles that inhibits hormone secretion and testosterone production, and is also known as hypogonadism. Depending on age, insufficient testosterone production can lead to abnormalities in muscle and bone development, underdeveloped genitalia, and diminished virility, libido and/or desire.

Testosterone deficiency in men (hypogonadism) may be present at birth (congenital) or may develop later (acquired). It is classified by the location of its cause along the hypothalamic-pituitary-gonadal axis:
Primary, disruption in the testicles
Secondary, disruption in the pituitary
Tertiary, disruption in the hypothalamus.

The most common congenital cause is Klinefelter's syndrome. This condition, which is caused by an extra X chromosome, results in infertility, sparse facial and body hair, abnormal breast enlargement (gynecomastia), and small testes.

Congenital hormonal disorders such as leutenizing hormone-releasing hormone (LHRH) deficiency and gonadotropin-releasing hormone (GnRH) deficiency (e.g., Kallmann's syndrome) also may cause testosterone deficiency.

Other congenital causes include absence of the testes (anorchism; also may be acquired) and failure of the testicles to descend into the scrotum (cryptorchidism).

Acquired causes of testosterone deficiency include chemotherapy; damage occurring during surgery involving the pituitary gland, hypothalamus, or testes; glandular malformation; head trauma that affects the hypothalamus; infection (e.g., meningitis, syphilis, mumps); isolated LH deficiency (e.g., fertile eunuch syndrome); radiation; testicular trauma; and tumours of the pituitary gland, hypothalamus, or testicles.

Androgen deficiency in women has been associated with an increased rate of sexual problems or complaints in a number of studies. These problems are frequently encountered in oophorectomized women and those with androgen deficiency from other causes. Hypoactive sexual desire disorder (HSDD) in women is the persistent or recurring deficiency (or absence) of sexual fantasies, thoughts and/or desire for, or receptivity to, sexual activity, which causes personal distress. The cause may be either physiological or psychological or a combination of both. Common physiological etiologies include hormone deficiencies, medications, and surgical interventions. Any disruption of the female hormonal milieu caused by these etiologies can result in decreased sexual desire. The lack of, or a decrease in, sexual desire may also be secondary to poor sexual arousal and response, or to pain associated with sexual activity. Another factor may be difficulty with inability to attain or maintain sufficient sexual excitement, a condition known as female sexual arousal disorder (FSAD).

The method of the invention may also be used in treatment of sexual dysfunction in men and women.

Normal daily production of testosterone in normal young men ranges from 3-10 mg per day with diurnal variation (maximum ~7 am declining throughout the day). The aim of testosterone therapy in men is to deliver physiologic amounts of testosterone to the systemic circulation producing serum testosterone levels within the normal range for healthy men (e.g. 300-1000 ng/dL or 10-35 nM).

Several clinical studies have demonstrated that in conditions such as female sexual dysfunction, testosterone administration, which is aimed at restoring testosterone levels to normal reproductive levels, is effective in improving sexual function. The studies to date suggest that systemic administration of doses ranging from 150 µg to 300 µg a day would be sufficient to return testosterone levels to mid- to high premenopausal levels in androgen deficient women.

The invention may be used in treating a wide variety of conditions responsive to testosterone therapy such as hypogonadism (primary and secondary), AIDS Wasting Syndrome, micropenis, somatopause, andropause, viropause, or androgen deficiency in adult males (ADAM), anaemia from renal dialysis or chronic kidney disease, benign prostatic hyperplasia, acne, diabetes, infertility, libido, periodontal disease, post-anabolic steroid abuse, dry eyes, diabetic retinopathy, retinopathy, and Lupus Erythematosis decreased bone density (i.e. osteoporosis), hyperlipemia, predisposition toward prostrate cancer, heart disease, angina, and hypertension.

When the composition of the invention and the composition used in the method of the invention includes a volatile solvent, one of the significant advantages of the preferred embodiment of the invention is that it dries rapidly, allows absorption of the active agent (particularly testosterone), and avoids the problems of accidentally dosing others by confining administration to axilla. The transdermal composition of the invention and the composition used in accordance with the method of the invention do not interfere with the application and use of other substances or products on the skin of a subject.

In the most preferred embodiment, the transdermal composition of the invention and the composition used in the method of the invention is applied as a lotion, spray or aerosol which is formulated to dry on the skin within three minutes of application. In this way we have found that the composition is driven into the skin and the testosterone composition forms a reservoir in the skin which we have found is particularly active in enhancing blood levels via the axilla without the undesirable effects associated with high localised subcutaneous testosterone levels in this region.

The compositions used in the method of the invention preferably have a drying time of less than three minutes. Drying time may be determined by in vitro or in vivo tests. A suitable in vitro test involves placing a 10 µL sample on a clean glass slide at room temperature (approx 20° C.) and using a four decimal place analytical balance the time take for the vehicle to stop evaporating is measured. The resulting drying times from three repetitions of the test may be averaged.

For in vivo drying time measurement 10 pLs applied to volar forearms (32° C.) of three subjects and the drying time is measured by touch and visual verification (no visible surface vehicle or shine).

The invention will now be described with reference to the following examples. It is to be understood that the examples are provided by way of illustration of the invention and that they are in no way limiting to the scope of the invention.

EXAMPLES

The examples are described with reference to the drawings.

Example 1

This example compares the single dose pharmacokinetics of testosterone following application of a single dose of a metered dose of a testosterone lotion to (a) the inner arm and (b) axilla, in healthy women.

In this example, the composition (referred to here as "Composition 1") contained the following components in the amounts by weight specified.

TABLE 1

| Component | Use | Concentration |
|---|---|---|
| Testosterone USP | Active | 1% w/v % |
| Octisalate USP | Penetration enhancer | 8% w/v |
| Povidone USP | Thickener | 1-5 w/v % |
| Purified water USP | Vehicle | 10% v/v |
| Isopropyl alcohol USP | Vehicle | 30% v/v |
| Alcohol USP | Vehicle | balance |

An open label, two period study was conducted in 12 healthy premenopausal women.

In each period, 1 mL of a metered dose testosterone lotion was applied as a single dose to either the inner arm or the axilla according to the randomisation schedule. Samples were collected over 72 hours for each subject and subsequently analysed for testosterone content.

Two women were withdrawn from the study prior to the first dosing period. Ten women completed the study and the results are presented in the graph shown in FIG. 1. The baseline corrected data comparing testosterone uptake from the axilla and the inner arm shows that the axilla has roughly a two fold increased uptake over the inner arm ($AUC_{0-72}$ was 5610.34 ng/dL/hr for the axilla compared to 2975.08 ng/dL/hr for the inner arm). No adverse sweating or odour was reported.

Example 2

This example investigated the cumulative testosterone permeation through human skin in vitro following deodorant spray application.

Finite-dose in vitro diffusion studies were undertaken using excised human, male abdominal skin whereby the deodorant was applied to the skin surface at pre-determined times after the topical application of a 5 µL dose of a testosterone lotion, formulated according to example 1. These experiments were performed over 24 hours using stainless steel, flow through diffusion cells based on those described previously (Cooper, E. R. *J. Pharm. Sci.* 1984, 73, 1153-1156) except that the cell was modified to increase the diffusion area to 1.0 cm$^2$. The formulations were applied using a finite dose technique (Franz, T. J. *Curr. Probl. Dermatol.*, 1978, 7, 58-68) to mimic clinical dosing conditions at an applied dose volume of 5 µL/cm$^2$. A piece of stainless steel wire mesh was placed directly below the skin in the receptor chamber of the of the diffusion cell to maintain a turbulent flow of receptor solution below the skin. The diffusion cells were maintained at a flow rate of approximately 1.0 mL/cm$^2$/hr by a microcassette peristaltic pump (Watson Marlow 505S UK). The cells were kept at 32±0.5° C. by a heater bar and the samples were collected into appropriately sized plastic vials on an automated fraction collector (Isco Retriever II, Lincoln, Nebr.) at specified intervals. The receptor solution (20% v/v EtOH in 0.002% w/v NaN$_3$) maintained sink conditions below the skin.

At designated, pre-determined time points following the application of the testosterone lotion, the following were applied:—
  one spray of a deodorant (containing isobutane, denatured alcohol, propane, triethyl citrate, partum, butane, and water) was applied to the skin surface for approximately 1 sec from a constant distance of ~10 cm from the top of the donor compartment of the cell; or
  3 µL of ethanol (the estimated amount of ethanol present in a 1 sec spray of deodorant).

The amount of testosterone that permeated the skin was quantified using a validated HPLC method.

The application of a spray of deodorant at different time points after the topical application of the testosterone lotion did not have a significant effect (enhancing or inhibitory) on the permeation of testosterone through human epidermis in vitro. Application of neat ethanol (EtOH) after testosterone lotion dosing also revealed no significant effect on the permeation of testosterone lotion through human epidermis in vitro.

Figure 2:
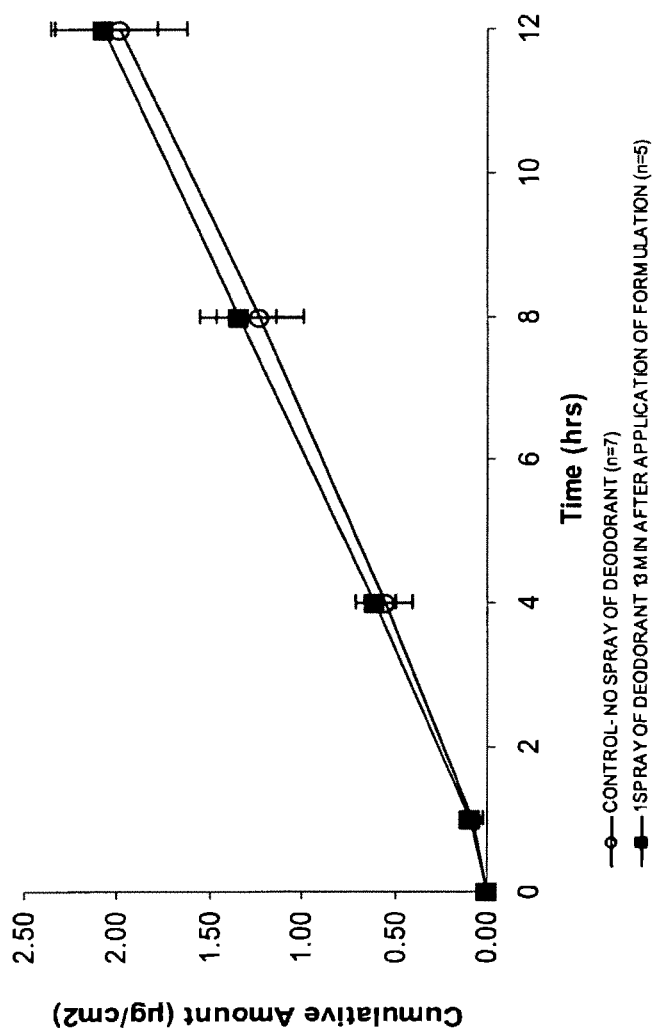
FIG. 2 is a graph of testosterone permeation profiles obtained after application of a deodorant spray to a composition according to one embodiment of the invention.
Figure 3:
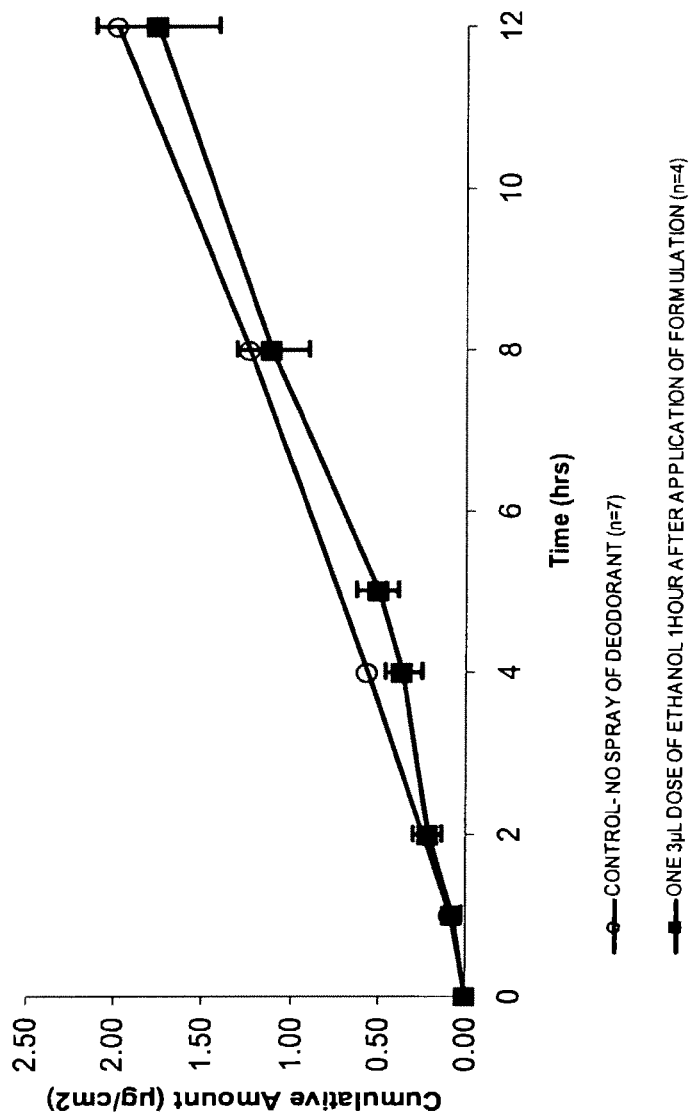
FIG. 3 is a graph of testosterone permeation profiles obtained after application of ethanol (3 μL) to the same embodiment of the invention as in FIG. 2.

FIG. 2 shows the testosterone permeation profiles obtained after application of deodorant spray to the formulation. FIG. 3 shows testosterone permeation profiles obtained after application of ethanol (3 µL) to the Composition 1 formulation. In both cases, it can be seen that the control line does not differ significantly along the time period examined.

The application of either a spray of deodorant or a finite-dose of neat EtOH did not appear to have an effect on the skin permeation of testosterone from a 5 µL dose of the lotion. Therefore it was concluded that the application of deodorant to the skin after application of the testosterone lotion will not impede transdermal penetration of testosterone.

Example 3

This example investigated the cumulative testosterone and estradiol permeation through human skin in vitro when included in a commercial deodorant Finite-dose in vitro diffusion studies were undertaken using heat-separated human, female abdominal epidermis. These experiments were performed over 24 hours using stainless steel, flow through diffusion cells based on those described previously (Cooper, E. R. *J. Pharm. Sci.* 1984, 73, 1153-1156) except that the cell was modified to increase the diffusion area to 1.0 cm$^2$. The formulations were applied using a finite dose technique (Franz, T. J. *Curr. Probl. Dermatol.*, 1978, 7, 58-68) to mimic clinical dosing conditions at an applied dose volume of 5 µL/cm$^2$. A piece of stainless steel wire mesh was placed directly below the skin in the receptor chamber of the of the diffusion cell to maintain a turbulent flow of receptor solution below the skin. The diffusion cells were maintained at a flow rate of approximately 1.0 mL/cm$^2$/hr by a microcassette peristaltic pump (Watson Marlow 505S UK). The cells were kept at 32±0.5° C. by a heater bar and the samples were collected into appropriately sized plastic vials on an automated fraction collector (Isco Retriever II, Lincoln, Nebr.) at specified intervals. The receptor solution (20% v/v EtOH in 0.002% w/v NaN$_3$) maintained sink conditions below the skin.

Two formulations were used that consisted of:—
  Composition 2: 1% w/v testosterone, 5% w/v octisalate, 32% v/v EtOH to 100% v/v Deodorant (Rexona Essentials for Men 'Dry' Antiperspirant Deodorant Spray, Unilever, Australia, BN: 6030 10793)
  Composition 3: 0.5% w/v E2 estradiol, 5% w/v octisalate, 52% v/v EtOH to 100% v/v Deodorant (Rexona Activreserve 'Classic Silk' Antiperspirant Deodorant Spray, Unilever, Australia, BN: 6054 11280)
  Note: extra ethanol was required in each of the formulations in order for the octisalate to remain miscible. The amount of ethanol differed between formulations as the deodorants used differed.

The amount of testosterone (TES) and estradiol (E2) that permeated the skin was quantified using a HPLC method.

Figure 4:
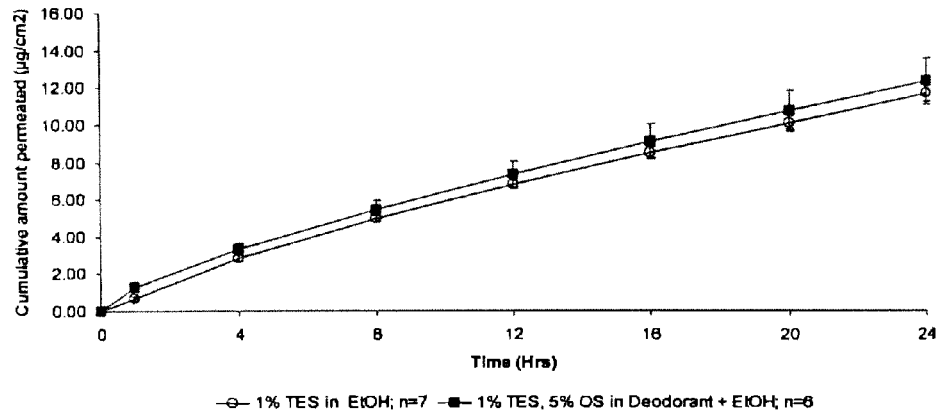
FIG. 4 is a graph of the testosterone permeation profiles obtained from the application of a different embodiment of the invention compared with application of a control.
Figure 5:
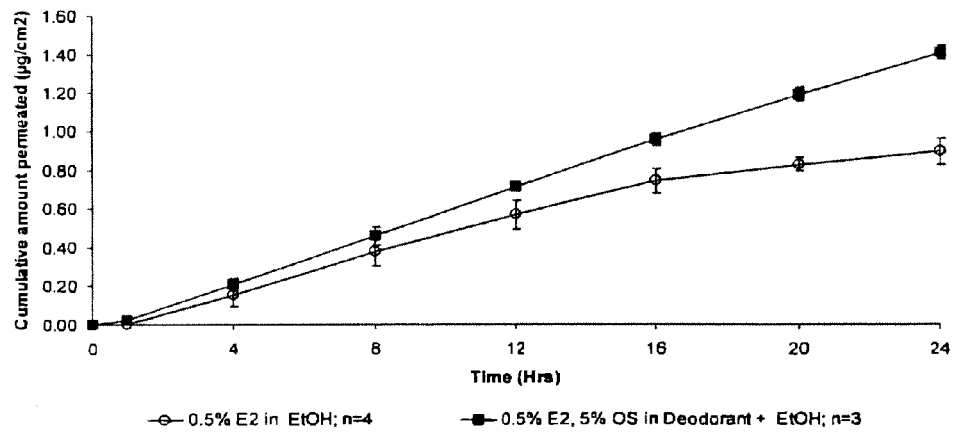
FIG. 5 is a graph of the estradiol permeation profile obtained from the application of another embodiment of the invention compared with application of a control.

The permeation of TES through human epidermis in vitro was unaltered when the drug was added, with octisalate (OS) in an EtOH solution, to a commercial deodorant compared to its permeation from an ethanolic solution without the penetration enhancer. FIG. 4 shows the TES permeation profiles obtained from the application of Composition 2 compared with application of a control. There is no significant difference in the curves produced. With composition 3, the permeation of E2 through human epidermis in vitro was significantly improved, when the drug was added, with OS in an EtOH solution, to a commercial deodorant compared to its permeation from an ethanolic solution without the penetration enhancer. FIG. 5 shows the E2 permeation profiles obtained from the application of Composition 3, compared with application of a control. The improved permeation is apparent after only 4 hours, and the difference becomes more significant with time particularly after 16 hours from dose.

The in vitro skin permeation of TES or E2 from an ethanolic solution comprised of OS and a commercial deodorant was therefore comparable to, if not higher than, its permeation from the ethanolic solutions comprised of the drug alone. This demonstrates that the addition of ingredients typically found in commercial deodorants to the formulations did not inhibit transdermal permeation of testosterone or estradiol.

Example 4

A study was conducted to assess the antiperspirant and deodorant characteristics of Composition 1 without added antiperspirant or deodorants. In this study, 16 male volunteers were asked to apply Composition 1 to their axilla(s) in a similar manner as in Example 1, and also to refrain from the use of other deodorants or antiperspirants on the axilla (armpits) that received Composition 1. The subjects were, however, instructed to apply deodorant if they were distressed with symptoms of sweating and to report such application. Interestingly, none of the subjects reported a need to use deodorant or antiperspirant when Composition 1 had been applied to the axilla.

Finally, various other modifications and/or alterations may be made without departing from the spirit of the present invention as outlined herein. The invention disclosed and defined in this specification extends to all alternative combinations of two or more of the individual features mentioned or evident from the text or drawings. All of these different combinations constitute various different aspects of the invention.

The invention claimed is:

1. A method of increasing the testosterone blood level of an adult male subject in need thereof, comprising applying to at least one axilla of the subject in a non-occlusive manner, a transdermal composition comprising:
   (a) testosterone;
   (b) from 40% to 99% v/v of volatile solvent selected from ethanol, isopropanol and mixtures thereof; and
   (c) from 0.01 to 15% w/v of octyl salicylate.

2. A method according to claim 1, wherein the composition further comprises from 1-5% w/v of thickener.

3. A method according to claim 2, wherein the thickener is polyvinylpyrrolidone.

4. A method according to claim 1, wherein the adult male subject is suffering from androgen deficiency.

5. A method according to claim 1, wherein the adult male subject is suffering from hypogonadism.

6. A method according to claim 5, wherein the testosterone is applied in an amount to provide a serum level in the range of from 300 to 1000 ng/dh.

* * * * *

UNITED STATES PATENT AND TRADEMARK OFFICE
CERTIFICATE OF CORRECTION

PATENT NO.        : 9,180,194 B2
APPLICATION NO.   : 14/509404
DATED             : November 10, 2015
INVENTOR(S)       : Tony Dipietro et al.

Page 1 of 1

It is certified that error appears in the above-identified patent and that said Letters Patent is hereby corrected as shown below:

IN THE CLAIMS

Column 24, Claim 6, line 17: please delete "of from 300 to 1000 ng/dh" to -- of from 300 to 1000 ng/dL --.

Signed and Sealed this
Fifth Day of April, 2016

Michelle K. Lee
*Director of the United States Patent and Trademark Office*